(12) United States Patent
Feasey et al.

(10) Patent No.: US 10,758,751 B2
(45) Date of Patent: Sep. 1, 2020

(54) RESPIRATOR

(71) Applicant: CLEAR AIR TECHNOLOGY LIMITED, Auckland (NZ)

(72) Inventors: Simon Vaughan Feasey, Auckland (NZ); Jeremy Mark Mauger, Auckland (NZ)

(73) Assignee: CLEAR AIR TECHNOLOGY LIMITED, Auckland (NZ)

( * ) Notice: Subject to any disclaimer, the term of this patent is extended or adjusted under 35 U.S.C. 154(b) by 0 days.

(21) Appl. No.: 15/768,272

(22) PCT Filed: Oct. 17, 2016

(86) PCT No.: PCT/NZ2016/050169
§ 371 (c)(1),
(2) Date: Apr. 13, 2018

(87) PCT Pub. No.: WO2017/065620
PCT Pub. Date: Apr. 20, 2017

(65) Prior Publication Data
US 2018/0296864 A1 Oct. 18, 2018

(30) Foreign Application Priority Data

Oct. 15, 2015 (NZ) .......................... 709617
Oct. 15, 2015 (NZ) .......................... 713259

(51) Int. Cl.
*A62B 18/00* (2006.01)
*A62B 18/02* (2006.01)
(Continued)

(52) U.S. Cl.
CPC ............ *A62B 18/003* (2013.01); *A61F 9/029* (2013.01); *A62B 18/006* (2013.01); *A62B 18/025* (2013.01); *A62B 23/02* (2013.01)

(58) Field of Classification Search
CPC ... A62B 18/003; A62B 18/006; A62B 18/025; A62B 9/06
See application file for complete search history.

(56) References Cited

U.S. PATENT DOCUMENTS 3,004,535 A 10/1961 Nielson
4,011,865 A 3/1977 Morishita
(Continued)

FOREIGN PATENT DOCUMENTS

BE 555402 A 2/1960
CN 103223214 A 7/2013
(Continued)

OTHER PUBLICATIONS

Wang (Air Curtain Study; https://www.amca.org/UserFiles/file/Energy%20Initiative%20Web%20Pages/Air%20Curtain%20Study(1).pdf; Published Jul. 25, 2014).*
(Continued)

*Primary Examiner* — Peter S Vasat
(74) *Attorney, Agent, or Firm* — Lowenstein Sandler LLP

(57) ABSTRACT

A mask or shield comprising a flow of positive pressure air directed through substantially opposing jets that creates a stream of laminar flow filtered air to create a turbulent air pocket therein for supplying filtered breathing air to a wearer's face and to exclude outside unpurified air. Also a mask or shield comprising a flow of positive pressure air directed via a powered impeller unit that is configured to distribute positively pressurised filtered breathable air inside the face mask in a substantially 360° plane or arc substantially parallel to the internal surface of the face mask and to exclude external unpurified air. The mask is separated from and does not form a seal around a wearer's face unless required such as in a deadly environment or malfunction.

18 Claims, 10 Drawing Sheets

(51) Int. Cl.
*A61F 9/02* (2006.01)
*A62B 23/02* (2006.01)

(56) References Cited

U.S. PATENT DOCUMENTS

| | | | | |
|---|---|---|---|---|
| 4,037,593 | A * | 7/1977 | Tate, Jr. | A41D 13/1115 128/201.17 |
| 4,136,688 | A | 1/1979 | Gorman | |
| 4,233,972 | A * | 11/1980 | Hauff | A62B 18/006 128/200.28 |
| 4,331,141 | A * | 5/1982 | Pokhis | A62B 18/006 128/201.25 |
| 6,119,689 | A * | 9/2000 | Korman | B01D 46/002 128/205.12 |
| 2005/0103343 | A1 * | 5/2005 | Gosweiler | A62B 18/006 128/206.12 |
| 2007/0240716 | A1 * | 10/2007 | Marx | A62B 18/006 128/204.21 |
| 2009/0210989 | A1 | 8/2009 | Becker et al. | |
| 2010/0031617 | A1 | 2/2010 | Ensor et al. | |
| 2011/0265790 | A1 | 11/2011 | Walker et al. | |
| 2015/0256010 | A1 | 9/2015 | Scandurra | |

FOREIGN PATENT DOCUMENTS

| | | |
|---|---|---|
| CN | 203724660 U | 7/2014 |
| CN | 103961822 A | 8/2014 |
| GB | 2251173 | 6/1995 |
| KR | 101460942 B1 | 11/2014 |
| WO | 2015167098 A1 | 11/2015 |

OTHER PUBLICATIONS

International Search Report and Written Opinion for International Application No. PCT/NZ2016/050169 dated Dec. 22, 2016, 20 pages.
International Preliminary Report on Patentability for International Application No. PCT/NZ2016/050169 dated Feb. 14, 2018, 19 pages.
Supplementary European Search Report for Application No. EP16855822 dated Jun. 13, 2019.
Partial English translation of the Office Action for Chinese Application No. 201680070468.5 dated Jan. 3, 2020, 11 pages.

* cited by examiner

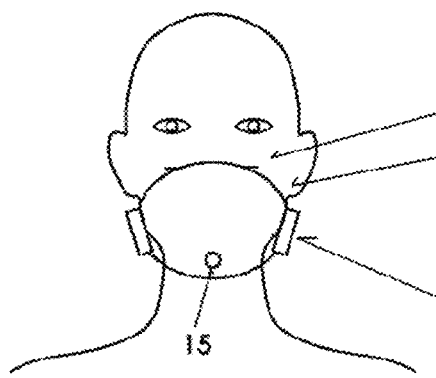
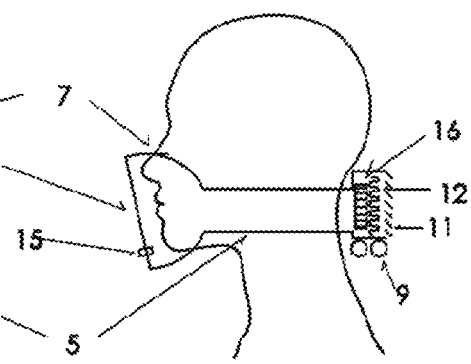
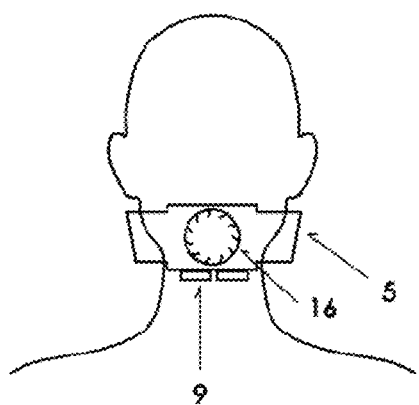

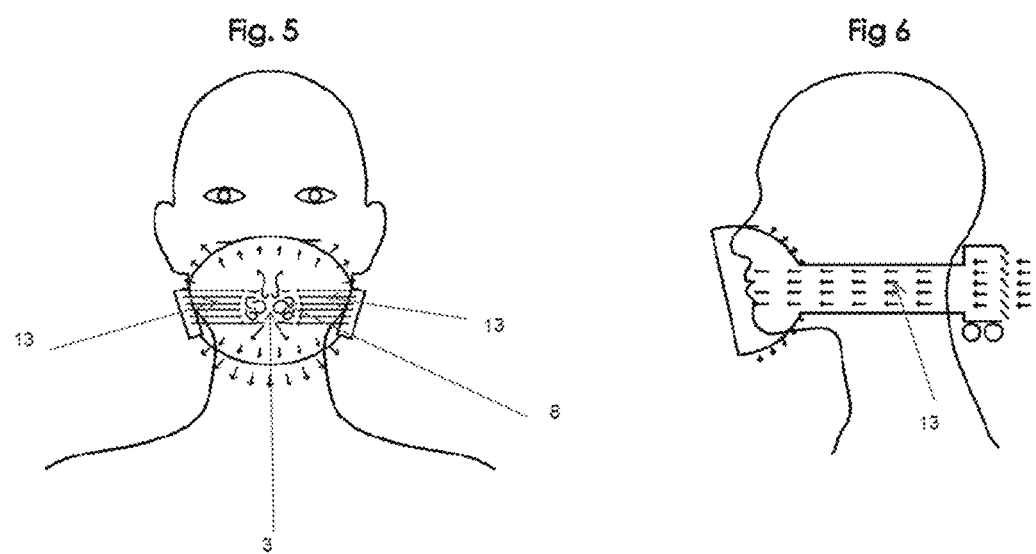

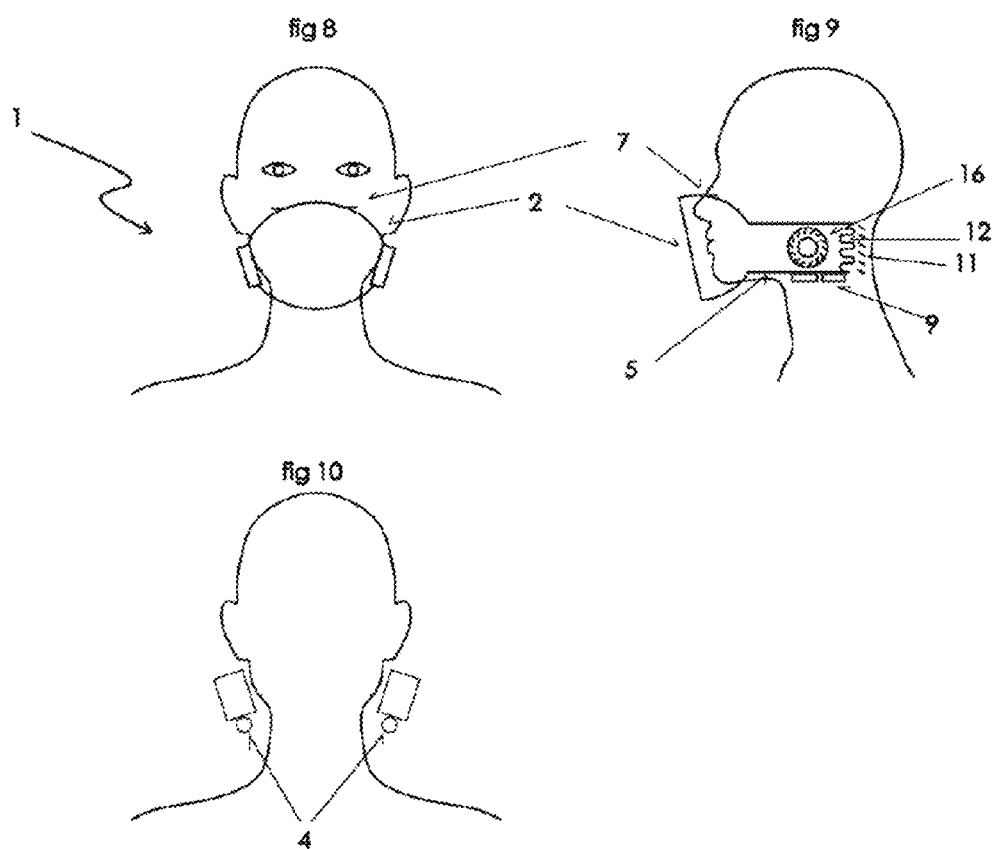

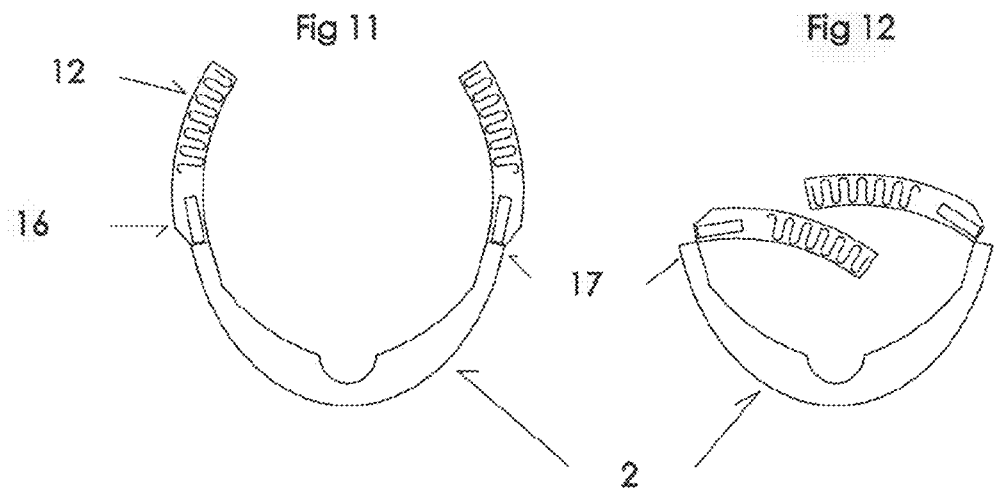
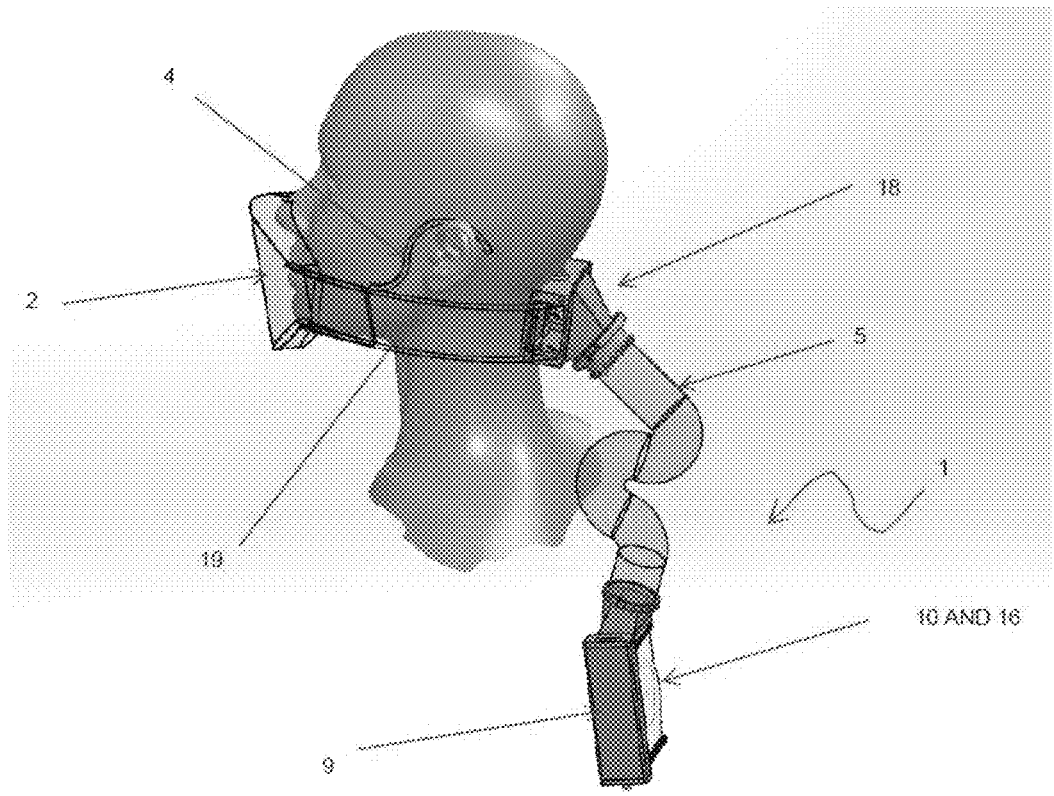
FIGURE 13

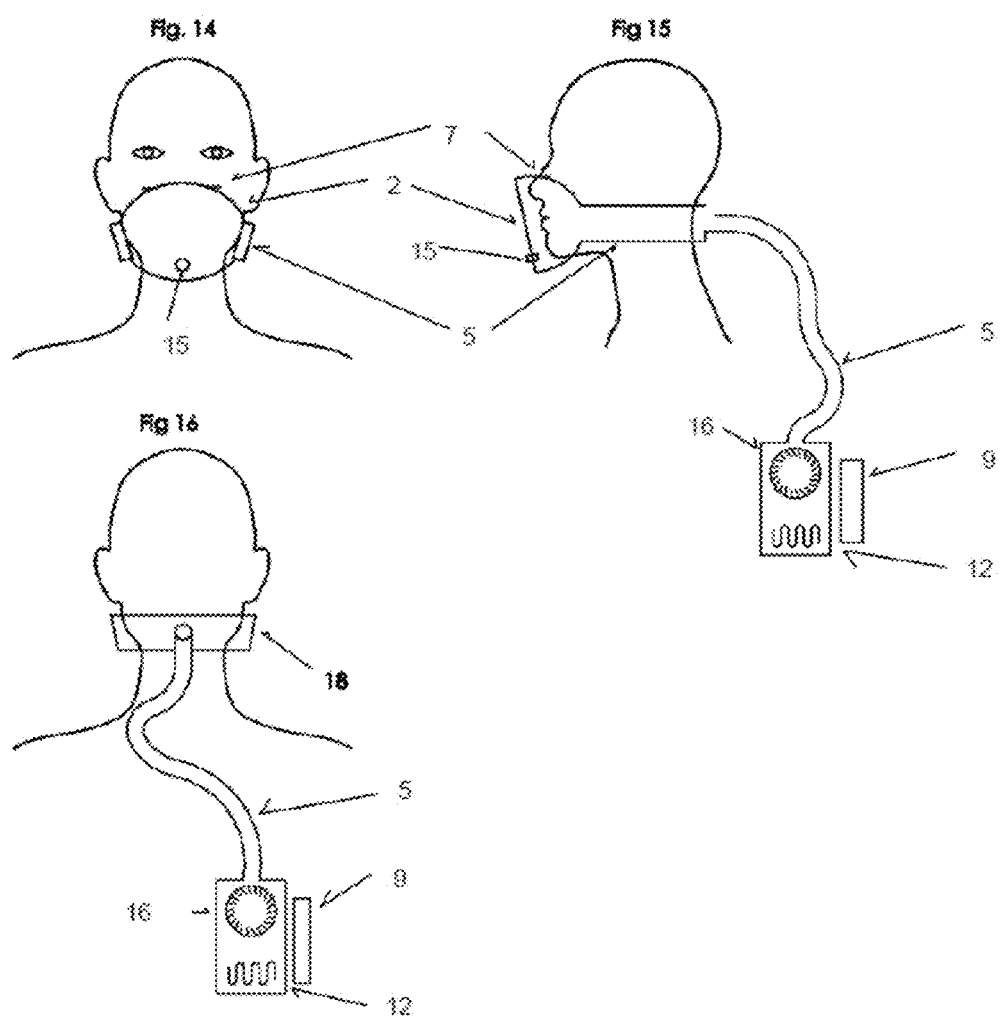

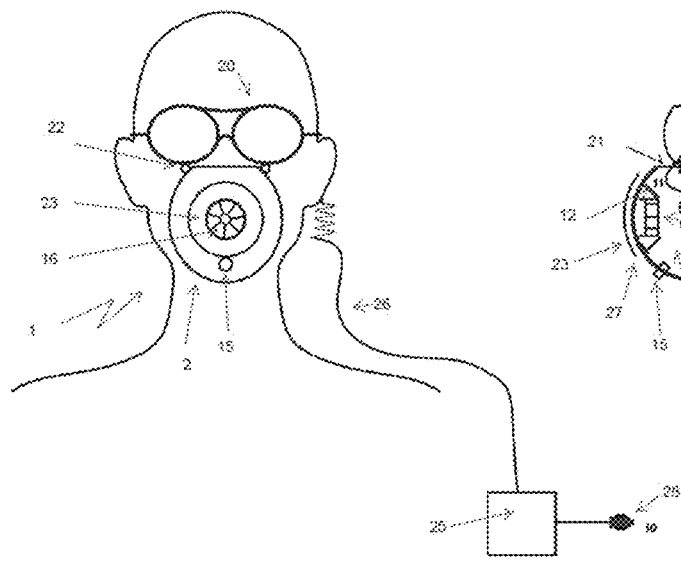
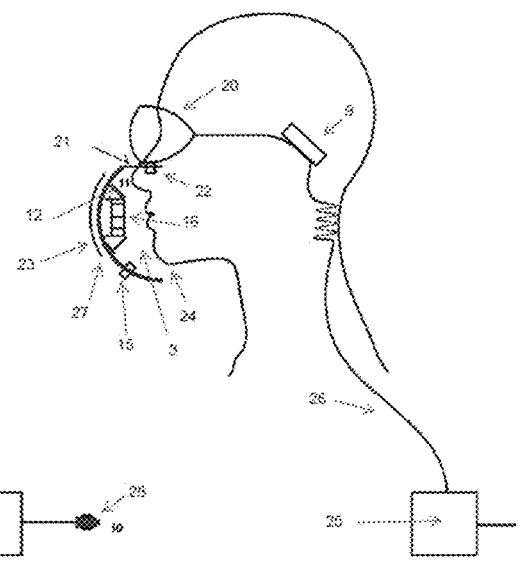
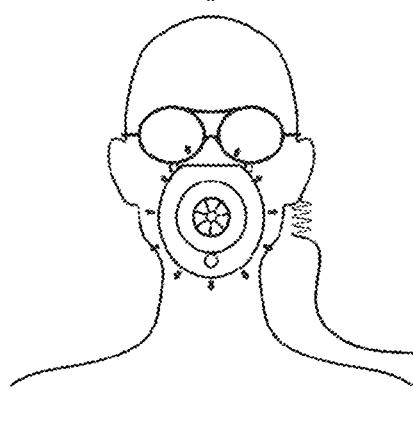
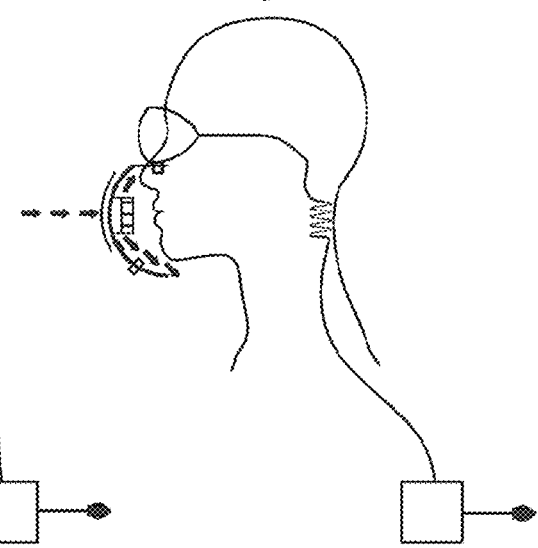

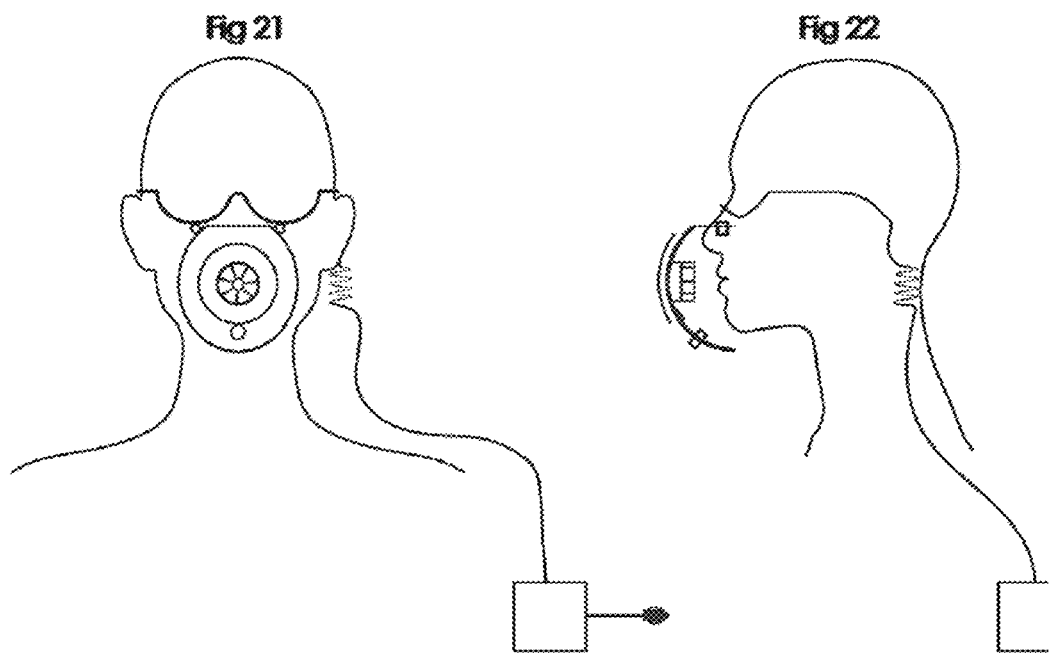
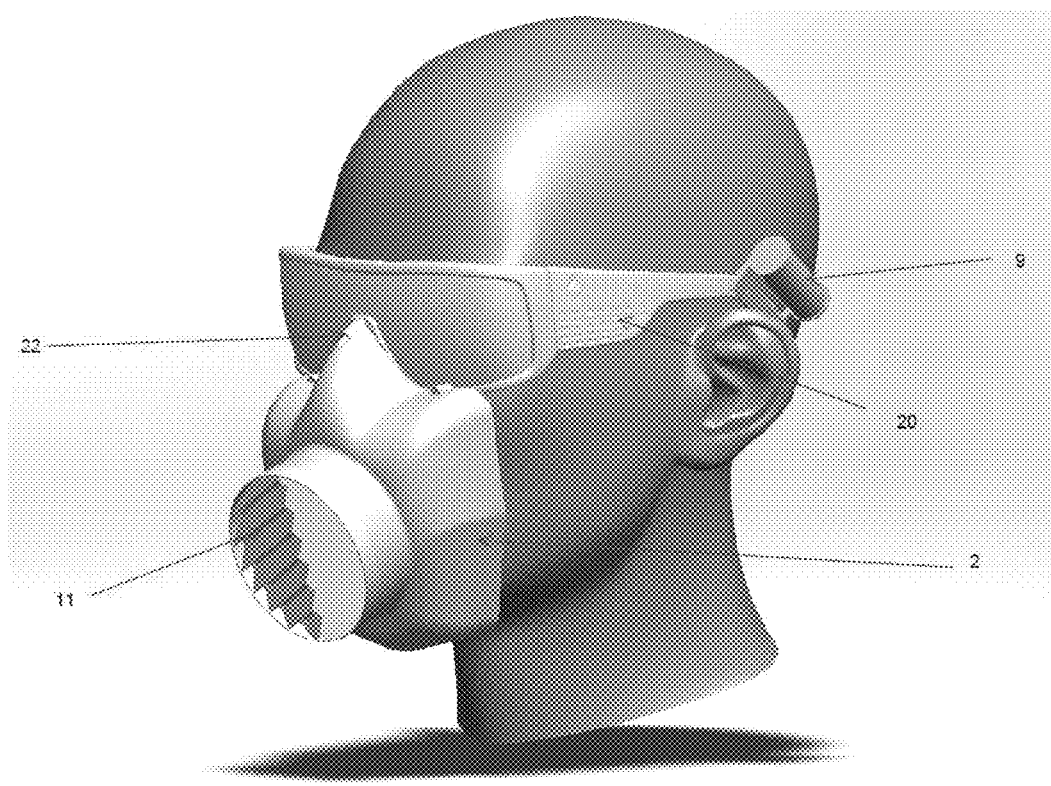
FIGURE 23

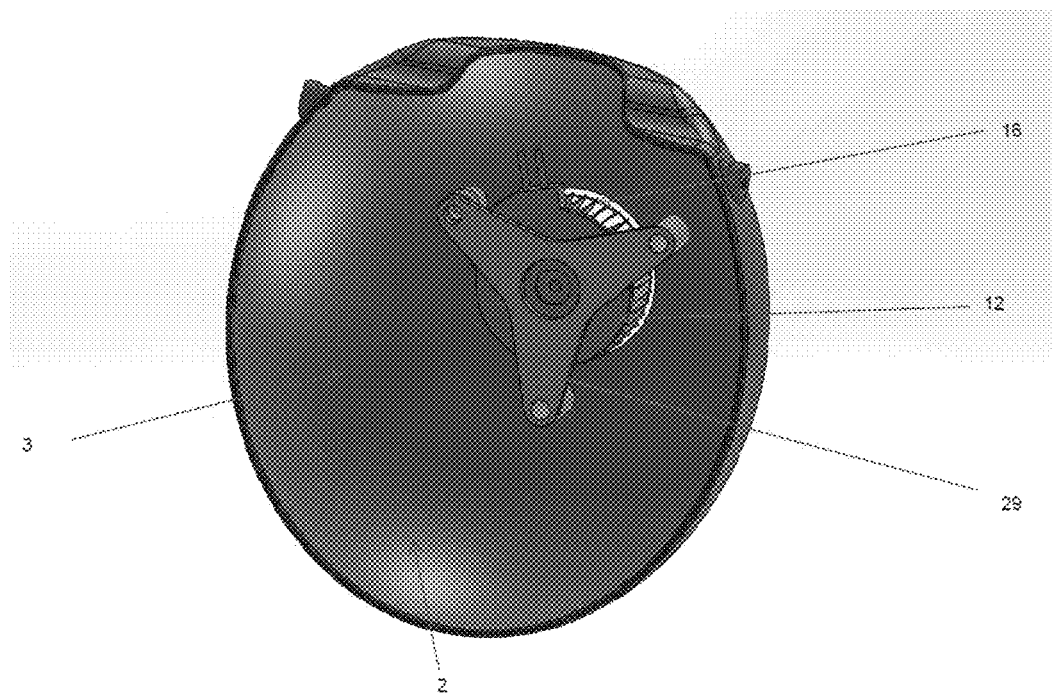
FIGURE 24
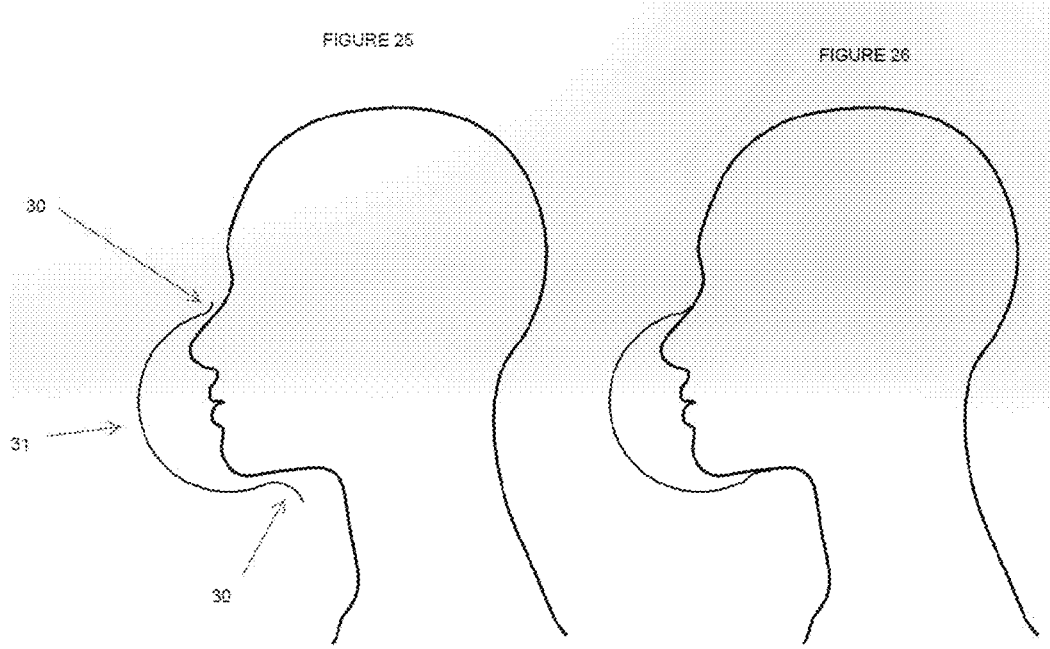

RESPIRATOR

RELATED APPLICATIONS

This application derives priority from New Zealand patent application numbers 709617 and 713259 incorporated herein by reference.

TECHNICAL FIELD

Described herein are respirators. More specifically, a mask or shield comprising a flow of positive pressure air directed through substantially opposing jets that creates a stream of laminar flow filtered air to create a turbulent air pocket therein for supplying filtered breathing air to a wearer's face and to exclude outside unpurified air. Also a mask or shield comprising a flow of positive pressure air directed via a powered impeller unit that is configured to distribute positively pressurised filtered breathable air inside the face mask in a substantially 360° plane or arc substantially parallel to the internal surface of the face mask and to exclude external unpurified air. The mask is separated from and does not form a seal around a wearer's face unless required such as in a deadly environment or malfunction.

BACKGROUND ART

The air we breathe contains varying amounts of particles such as dust, dirt pollen, smog and noxious fumes. Air pollution is fast becoming one of the largest health threats of the industrial world. Lung cancer and cardiovascular disease are increasing because of factory and vehicle air pollution where recent studies have shown lung cancer is two to three times more common in cities than in the countryside despite similar rates of tobacco smoking. Workers in certain industrial or agricultural operations are exposed to toxic dusts, mists and fumes which can cause illness or death even if inhaled in relatively small quantities over a period of time.

Many persons, because of their jobs, lifestyle or location, must expose themselves to airborne particulate matter or fumes that are allergenic, or which can be injurious to their health. The size of the particles is a main determinant of where in the respiratory tract the particle will come to rest when inhaled. Larger particles are generally filtered in the nose and throat via cilia and mucus, but particulate matter smaller than about 10 micrometres, referred to as $PM_{10}$, can settle in the bronchi and lungs and cause health problems. The 10 micrometre size does not represent a strict boundary between respirable and non-respirable particles, but has been agreed upon for monitoring of airborne particulate matter by most regulatory agencies. Because of their small size, particles in the order of ~10 micrometres or less ($PM_{10}$) can penetrate the deepest part of the lungs such as the bronchioles or alveoli.

Similarly, so-called fine PM, particles smaller than 2.5 micrometres, $PM_{2.5}$, tend to penetrate into the gas exchange regions of the lung (alveolus), and very small particles (<100 nanometres) may pass through the lungs to affect other organs.

Some persons are allergic to certain pollens or dust occurring naturally in the air and manifest this by an allergic reaction known as Hay Fever. Quite often, if uncontrolled, this allergic reaction progresses to a serious sinus condition or asthma. Also, the purity or quality of air may be affected by the presence of infectious airbourne contaminates.

Face masks are used to combat air pollution and contaminates that affect the quality of air. A conventional face mask is usually manufactured out of a piece of material that aims to filter out particulate material and seals or contacts against the face. One example is a mask that is manufactured out of cotton material, with lots of leakage around the face and within the mask, the filter either being just a tiny square inside the cotton mask or the entire mask itself. Nevertheless these types of mask are not particularly effective at filtering out particulate matter. Furthermore, these types of mask may only address air particulates and not noxious gases. Also, as the mask contacts the face, this is uncomfortable for a wearer and some skin types are sensitive to conventional mask material and extended use can create skin irritation and even skin damage. Even users with non-sensitive skin may develop skin irritations from face mask contact.

A mask that contacts the face of a user with facial hair can not form an effective seal due the facial hair forming a barrier between the mask and skin contact surface. In fact, a study on the effect of facial hair on the face seal of negative-pressure respirators has shown at least a 330 fold drop in protection of a dust mask when used with a beard. Results such as this indicate that the presence of a beard greatly increases the leakage through the respirator face seal, and this leakage should not be permitted when users are required to wear respirators. Furthermore, wearing a conventional mask makes communication difficult both audibly and visually.

Style is also a consideration for a wearer and some prior art masks are bulky and those considered to be unaesthetically pleasing to the eye are less likely to be worn.

Conventional respiratory filter masks are often worn by people who are exposed to airborne particulate matter or noxious gases or fumes to avoid inhaling these harmful substances. In order to achieve an effective efficiency and an unencumbering resistance to airflow, conventional respiratory filter masks are cumbersome and of a design that makes them impractical for everyday use. For example, wearing one of these face mask filters is very uncomfortable with necessarily tight-fitting head straps and face mask seals. Notwithstanding that, all people's faces are different in shape making it difficult to achieve a positive seal with the prior art models. In addition, the wearer of one of these masks must forcefully inhale against the pressure drop of the air passing through the filter media and when exhaling must force the air out through an exhaust valve. After a period of time this can become uncomfortable to normal people and exhausting to those with respiratory problems.

Full face coverage filter masks that do cover the eyes in addition to nose and mouth are often prone to fogging of the transparent face shield and are even more uncomfortable to wear. As above, speech and sight are greatly impaired and bulky hoses and filter cartridges are cumbersome and unsightly to wear. In fact prior art face mask filter respirators are so cumbersome and uncomfortable that many people (including allergy suffers) risk the health hazards involved rather than wear this type of protection.

From the above, it can be seen that there is a need for an improved flow or face mask that overcomes disadvantages of known face masks or at least provides the public with a useful choice.

Further aspects and advantages of the process and product will become apparent from the ensuing description that is given by way of example only.

SUMMARY

Described herein are respirators. More specifically, a mask or shield comprising a flow of positive pressure air directed through substantially opposing jets that creates a stream of laminar flow filtered air to create a turbulent air pocket therein for supplying filtered breathing air to a wearer's face and to exclude outside unpurified air. Also a mask or shield comprising a flow of positive pressure air directed via a powered impeller unit that is configured to distribute positively pressurised filtered breathable air inside the face mask in a substantially 360° plane or arc substantially parallel to the internal surface of the face mask and to exclude external unpurified air. The mask is separated from and does not form a seal around a wearer's face unless required such as in a deadly environment or malfunction.

In a first aspect there is provided a respirator comprising:
a face shield with an attachment means for attaching the face shield to a face region of a wearer;
at least two substantially opposing air supply lines in fluid communication with each side of the face shield to provide a positive stream of laminar flow of air; and
an air filter for filtration of the laminar flow of air;
wherein the at least two opposing air supply lines are spaced apart and directed to allow streams of the laminar flow of filtered air to collide at an intersection region within a cavity of the face shield creating a turbulent flow of air that radiates away from the intersection region therein for supplying filtered breathing air to a wearer's face region and exclusion of outside unpurified air, and wherein the face shield does not form a seal around the face region of the wearer.

In a second aspect there is provided a respirator comprising:
a face mask configured to cover the face of a user; and
at least one air filter attached to the face mask and configured to filter unpurified air to provide breathable air;
wherein
the respirator also comprises a powered impeller unit mounted on the face mask and configured to compress and distribute the breathable air inside the face mask in an arc substantially parallel to the internal surface of the face mask; and
the face mask forms a gap between an edge of the face mask and the user's face and configured to allow a positive flow of the breathable air together with exhaled air to exit the face mask and exclude ingress of external unpurified air.

In a third aspect there is provided a respirator comprising:
an air delivery system for generation of a positive flow of air;
a face mask configured to cover the face of a user; and
the face mask forms a gap between an edge of the face mask and the user's face and configured to allow the positive flow of breathable air together with exhaled air to exit the face mask and exclude ingress of external unpurified air;
wherein
the gap between the edge of the face mask and the user's face closes to form a seal when air pressure inside the mask drops to a predetermined level.

Advantages of the above include a respirator with portable air delivery system or where the air delivery system is integrated into the mask for compactness. The face shield is removable and manufactured out of a non porous material so that the face shield is easily cleaned and does not absorb gases or other types of pollutants. Also, no condensation forms as there is a positive flow of air and an engineered gap area for bleed air to the exterior or design spaces. In this way, the face mask is hygienic and once cleaned can be shared between different users. The material of the face shield is dynamically flexible or rigidly solid, interchangeable and moulded to accommodate different sized faces or to aesthetically alter the look of the shield. A moulded interior surface of the face shield allows directional flow of air emanating from the centre of the cavity of the face shield to radiate out thereby preventing a venturi effect entraining outside air, and provides a control of bleed air to the exterior or design spaces. Also, the moulded interior surface of the face mask allows directional flow of air emanating from the impeller unit to radiate out in a substantially 360° plane or arc substantially parallel to the internal surface of the face mask but not directly at the user's mouth and nose. In this way, a pocket of purified air in front of the mouth and nose is provided whilst also allowing for exhaled air to escape. An advantage of the interior mould surface is that it controls the direction of the bleed of air such that there is no high speed air blowing into eyes of the wearer. A hollow section of the arm provides an attachment point for the integral air supply line to the face shield thereby minimising components of the respirator and hence reduced manufacturing costs and a more streamlined aesthetic appearance. The arm is foldable to allow for ease of storage when the respirator is not in use. There is a mechanism for adjustment for both width and length of the arms that rest on top of the ear. In this way, the fitment of the face shield is easily accommodated to suit the size and shape of a wearer's face. The attachment points utilise a releasable attachment means such as a user's eyewear. The attachment means provides a conduit for electrical wiring from a power source, and the attachment points provide the functionality of an electrical connection between the power source and the powered impeller unit. Therefore, the attachment points support and centre the face mask on a face region of a user, wherein the face mask does not contact the face region nor form a seal around the face region of the user.

Advantages of a face mask or shield that does not require a seal are that it does not contact the skin (no skin irritation and hence more comfortable to wear), the face mask does not need to be monitored to ensure a positive seal to keep out pollutants, and the wearer does not have to forcefully inhale or exhale against the pressure drop associated with a sealed system.

Furthermore, wearers with facial hair can benefit from this face shield unlike conventional masks where a positive seal is required. As above, an engineered cavity within the mask and gap area is advantageously dimensioned to optimise supply air flow and bleed velocity such that a pocket of purified air in front of the mouth and nose is created whilst also allowing for exhaled air to escape. The design also controls the direction of the bleed air so that there is no high speed air blowing into the eyes. The minimal design of the components of the respirator reduces manufacturing costs and provides a more streamlined aesthetic appearance.

A further advantage is that the motor and the pressure sensor are very close to the mouth and nose. When the user takes a sharp inhalation of breath, the close proximity of the motor and the very small air column enable the system to respond very quickly to maintain positive pressure, and ensure that the direction of the air flow is not reversed by breathing in.

BRIEF DESCRIPTION OF THE DRAWINGS

Further aspects of the respirator apparatus, operation and uses thereof will become apparent from the following description that is given by way of example only and with reference to the accompanying drawings in which:

Respirator with Rear Integrated Air Delivery System

FIG. 2 illustrates a front schematic view of the same respirator of FIG. 1;

FIG. 3 illustrates a side view of the same respirator of FIGS. 1 and 2;

FIG. 4 illustrates a rear schematic view of the respirator of FIGS. 1, 2 and 3;

FIG. 5 illustrates a front schematic drawing of the air flow within the cavity of the face shield of the respirator showing laminar to turbulent flow; and FIG. 6 illustrates a side schematic drawing of the air flow within a cavity of the face shield of the respirator.

Respirator with Dual Integrated Air Delivery Systems

Figure 7:
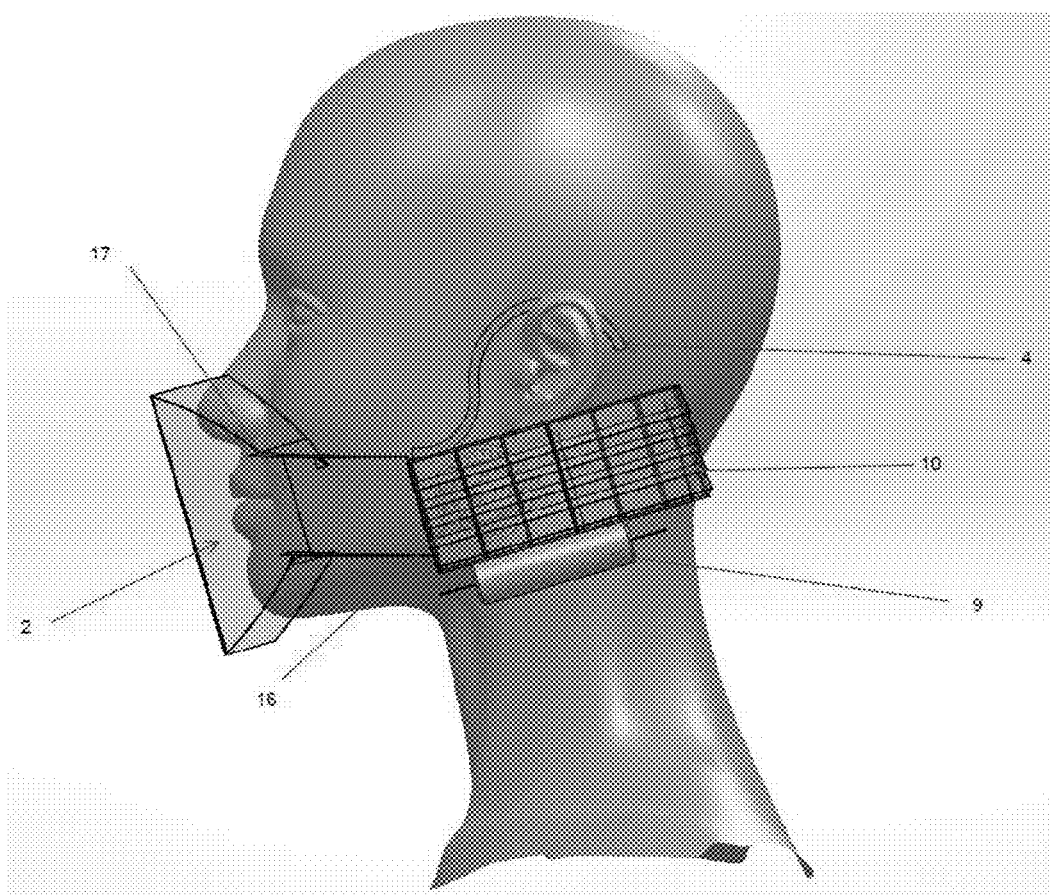

FIG. 7 illustrates a rendered side view of one preferred embodiment of a respirator with dual integrated air delivery system being worn by a user;

FIG. 8 illustrates a front schematic view of the same respirator of FIG. 7;

FIG. 9 illustrates a further side view of the same respirator of FIGS. 7 and 8;

FIG. 10 illustrates a rear schematic view of the respirator of FIGS. 7, 8 and 9;

FIG. 11 illustrates a top schematic view of the respirator with dual air delivery system with air tube and arms in the unfolded position;

FIG. 12 illustrates a top schematic view of the respirator of FIG. 11, but with the air tube and arms in the folded position.

Respirator with Separate Air Delivery System

FIG. 13 illustrates a rear perspective view of a further embodiment of a respirator with separate air delivery system being worn by a user;

FIG. 14 illustrates a front view of the same respirator of FIG. 13;

FIG. 15 illustrates a side profile view of the respirator of FIGS. 13 and 14;

FIG. 16 illustrates a rear view of the same respirator of FIGS. 13 to 15.

Respirator with Front Integrated Air Delivery System

FIG. 17 illustrates a side view of a further preferred embodiment of a respirator with front mounted impellor being worn by a user with full frame safety glasses attached;

FIG. 18 illustrates a front view of the same respirator of FIG. 17;

FIG. 19 illustrates a front view of the same respirator of FIGS. 17 and 18 with radial direction of air flow as indicated between mask and face;

FIG. 20 illustrates a side view of the same respirator of FIGS. 17 to 19 with direction of air flow as indicated within a cavity;

FIG. 21 illustrates a front view of the same respirator of FIGS. 17 to 20 with half-frame eyewear attached to the face mask;

FIG. 22 illustrates a side view of the same respirator of FIG. 21 with half-frame eyewear attached to the face mask;

FIG. 23 illustrates a side perspective schematic view of the same respirator of FIGS. 17 to 20 with protective eyewear attached to the face mask; and FIG. 24 illustrates the internal cavity of the face mask of the respirator of FIGS. 17 to 23.

Respirator with Floating Seal

FIG. 25 illustrates a side schematic view of another embodiment of a respirator with a floating seal in an open position; and FIG. 26 illustrates a side schematic view of the respirator of FIG. 25 with the floating seal in a closed position.

DETAILED DESCRIPTION

As noted above, described herein are respirators. More specifically, a mask or shield comprising a flow of positive pressure air directed through substantially opposing jets that creates a stream of laminar flow filtered air to create a turbulent air pocket therein for supplying filtered breathing air to a wearer's face and to exclude outside unpurified air. Also a mask or shield comprising a flow of positive pressure air directed via a powered impeller unit that is configured to distribute positively pressurised filtered breathable air inside the face mask in a substantially 360° plane or arc substantially parallel to the internal surface of the face mask and to exclude external unpurified air. The mask is separated from and does not form a seal around a wearer's face unless required such as in a deadly environment or malfunction.

For the purposes of this specification, the term 'about' or 'approximately' and grammatical variations thereof mean a quantity, level, degree, value, number, frequency, percentage, dimension, size, amount, weight or length that varies by as much as 30, 25, 20, 15, 10, 9, 8, 7, 6, 5, 4, 3, 2, or 1% to a reference quantity, level, degree, value, number, frequency, percentage, dimension, size, amount, weight or length.

The term 'substantially' or grammatical variations thereof refers to at least about 50%, for example 75%, 85%, 95% or 98%.

The term 'comprise' and grammatical variations thereof shall have an inclusive meaning—i.e. that it will be taken to mean an inclusion of not only the listed components it directly references, but also other non-specified components or elements.

The term 'respirator' or grammatical variations thereof refers to a powered air-purifying respirator (PAPR). The purpose of a PAPR is to take air that is contaminated with one or more types of pollutants, remove a sufficient quantity of those pollutants and then supply the air to the user. A PAPR may comprise a powered fan which forces incoming air through one or more filters for delivery to the user for breathing. The fan and filters may be carried by the user or the air may be fed to the user via tubing while the fan and filters are remotely mounted.

The term 'face shield' or grammatical variations thereof refers to a component or device of the respirator used to protect a wearer's face (or part thereof) from external pollutants or particulates and direct purified air in front of the mouth and nose whilst also allowing for exhaled air to escape. Throughout the specification, the face mask or shield may also be referred to as an Air Focusing shield (AFS).

The term 'powered impeller unit' refers to a rotor and associated motor used to increase the pressure and flow of air from a filter into the internal cavity of a face mask.

The term 'positive stream of laminar flow of air' or grammatical variations thereof refers to a positive pressure of air where the fluid or air flows in substantially parallel layers, with no disruption between the layers. This is in contrast to turbulent flow which is a less orderly flow regime that is characterised by eddies or small packets of fluid particles which result in lateral mixing.

The term 'positive flow' or grammatical variations thereof refers to a laminar flow of air created by the powered impeller unit into the internal cavity of the face mask and out of the gap between an edge of the face mask and the user's face. This laminar flow of air provides a constant supply of filtered breathable air for the user and excludes lateral mixing of unpurified external air in the face mask from the gap. This is in contrast to turbulent flow which is a less orderly flow regime that is characterised by eddies or small packets of fluid particles which results in lateral air mixing.

The term 'gap area' or grammatical variations thereof refers to an engineered area between the skin surface and the face mask when positioned at a face region of a wearer. This may be calculated by the average gap distance of the mask edge from the skin surface multiplied by the mask edge perimeter. It should be understood by those skilled in the art that the gap distance from the skin surface may vary due to a number of factors, for example mask design and variation in contours of a user's face.

The term 'cavity' or grammatical variations thereof refers to an engineered internal space between the skin surface and the face mask at a region where laminar flow of air is directed to intersect.

In a first aspect there is provided a respirator comprising:
a face shield with an attachment means for attaching the face shield to a face region of a wearer;
at least two substantially opposing air supply lines in fluid communication with each side of the face shield to provide a positive stream of laminar flow of air; and
an air filter for filtration of the laminar flow of air;
wherein the at least two opposing air supply lines are spaced apart and directed to allow streams of the laminar flow of filtered air to collide at an intersection region within a cavity of the face shield creating a turbulent flow of air that radiates away from the intersection region therein for supplying filtered breathing air to a wearer's face region and exclusion of outside unpurified air, and wherein the face shield does not form a seal around the face region of the wearer.

The face shield may be removable and manufactured out of a non porous material. In this way, the face shield can be easily cleaned and may not absorb gases or other types of pollutants. Also, the material of the face shield may be dynamically flexible or rigidly solid as required. This allows the face shield to be easily interchanged and moulded to accommodate different sized faces and with the ability to aesthetically alter the look of the shield. For example, a face shield manufactured out of transparent material may allow a wearer to easily communicate with others with both visual and vocal expression.

The face shield may include a moulded interior surface that allows a flow of air directed within the cavity of the face shield to radiate out to the peripheral edges of the face shield thereby preventing a venturi effect entraining outside air and provides a control of bleed air to the exterior. In this way, a pocket of purified air is provided in front of the mouth and nose whilst also allowing for exhaled air to escape.

The interior mould surface may control the direction of the bleed of air such that there is no high speed air blowing into eyes of the wearer.

The attachment means may include an arm member or temple that extends over the ear to help hold the face shield in place.

The arm may include a separate or integrated earpiece that covers the portion of the arm that rests on top of the ear. The earpiece provides added comfort to the wearer.

The arm or side member may be hollow to provide an integrated air supply line to the face shield. In this way, the components of the respirator may be minimised providing for reduced manufacturing costs and a more aesthetic streamlined appearance.

The arm may be foldable to allow for ease of storage when the respirator is not in use.

The face shield may include a mechanism for adjustment for both width and length of the arms that rest on top of the ear. In this way, the fitment of the face shield can be easily adjusted to suit the size and shape of a wearer's face.

A further attachment means may include a nose piece that helps keep the face shield in a required position on the wearer's face region.

The above attachment means of two arms and a nose piece provide an attachment point to support and retain the face shield on a face region of a wearer, wherein the face shield does not contact the face region nor form a seal around the face region of the wearer. Advantages of a face shield that does not require a seal are that it does not contact the skin (no skin irritation and hence more comfortable to wear), the face shield does not need to be monitored to ensure a positive seal to keep out pollutants, and the wearer does not have to forcefully inhale or exhale against the pressure drop associated with a sealed system. Also, the above attachment points do not require contact to hair or top of the head, for increased comfort.

The air supply line may be a flexible hose attached to a pump housing configured to extend up a back, head or under a chin of the wearer. It should be appreciated by those skilled in the art that any type of flexible air hose may conceivably be used with this invention. For example, this may include, but not be limited to, clear silicon air line.

The flexible airline may include a manifold, Y-piece adaptor or twin coupling air line three-way splitter to allow a dual air line configuration for integration into each arm member or on either side of the wearer's head. In this way, a positive stream of laminar flow of air may be provided on each side of the face shield.

In one embodiment, a first jet nozzle may be spaced at an engineered distance apart from a corresponding second jet nozzle attached to distal ends of air lines such that a positive stream of laminar flow is directed to the intersection region within the cavity of the face shield. In this way, the jet nozzles are dimensioned and positioned such that they may not venturi external air into the cavity, but any venturi effect that may occur only recirculates purified air within the cavity. Optionally, the positive stream of laminar flow may be regulated, in part, by adjusting the area of the nozzle opening, to more or less restrict the air flow and thereby increase or decrease the positive pressure inside the face shield.

It is envisaged that the dynamic pressure or positive pressure within the engineered gap area of the face shield may range from 1-20 Pa. The inventor has found that an optimum pressure may be 5 Pa as the respirator allows for a continuous supply of purified air in the gap space and there is no requirement of a high positive pressure. However, this should not be seen as a limitation on the embodiments envisaged for this invention. If the outside air becomes more hazardous to the wearer and/or this outside air becomes more turbulent or "windy", then the positive pressure of the filtered air within the gap space of the face shield may be increased in order to prevent possible infiltration of the outside air. Conversely, the pressure may be decreased depending on ambient conditions.

The gap area may range from 10-100 $cm^2$, wherein the gap area may be calculated from a supply air flow and bleed velocity respectively.

The supply air flow from a pump may range from 1-9 L/s or 0.001-0.009 m³/s. The inventor has found that an optimum air flow may be 2-3 or up to 7 L/s or 0.002-0.003 up to 0.007 m³/s. By way of example, an over-supply of air given heavy breathing may be considered to be approximately 0.5 L/s. It should be appreciated by those skilled in the art that the air supply should always be above the peak inhalation, i.e. an oversupply such that the outflowing direction of the air gap is not reversed.

The respirator may also comprise at least one air pressure sensor attached to the mask and configured to monitor air pressure inside and outside the mask to send an electrical signal to an impeller unit motor to vary the amount of power to the impeller rotor thereby controlling the speed of the impeller rotor to maintain positive air pressure within the interior cavity of the face mask.

As above, the bleed velocity may be dependent on the area of the gap space. For example, the bleed velocity correlating to a particular gap space may be 0.5 m/s:100 cm², 1 m/s:50 cm² or 2 m/s:25 cm² respectively.

The respirator may include an air delivery system or fan supply unit comprising an electric motor, filter assembly and impeller or fan to create an air pump. In this way, a positive pressure flow of air may be delivered to the respirator. The air flow and positive pressure may be regulated, in part, by adjusting the fan speed.

The air delivery system may be attached to a wearer's pocket, mounted on the back of a wearer's head or fastened to a belt or some other convenient place by fastener such as a clip. In some instances, and depending on advancement in electronic technology, the air delivery system may be integrated into the face shield or other components of the respirator itself.

The air delivery system may include two or more air delivery systems i.e. motor, fan and filter assemblies mounted on either side of a wearer's head.

The fan supply unit may be powered by a battery or batteries. The battery may be rechargeable or replaceable and be of sufficient capacity to allow the respirator to operate for a desired period of time. The battery or batteries may be mounted to the air delivery system itself or may be worn elsewhere on a body with power being sent via a cable or other such means.

The air delivery system may include a filter media or a filtration system. The filtration system may include a breather shield for protection against the elements such as rain.

The filter media may include a three stage filtration system or mechanism where particulate and gas phase removal may be effected by use of composite filters and combinations thereof for different applications. For example, filtration mechanisms may include, but not be limited to, adsorption, absorption, size exclusion, interception, inertial impactment, electrostatic attraction and diffusion (Van der Waals forces).

The discharged air from the fan supply unit may pass through the filter media and in doing so, any particulate matter, i.e. dust, pollen, etc. in the air may be retained on or in the filter media, at least down to the particle size limitation of the filter media used. The filter media used generally may be that with maximum porosity and yet may retain a sufficient percentage of the minimum size of the offending particles the wearer may want to avoid. In this way, the filter has the least resistance to air flow and therefore may require the least fan and power requirements and thereby the least size and weight overall, hence the filter media may be interchangeable and/or removable.

The filtration efficiency of the filter media or mechanism may at least meet applicable industry standards by those skilled in the art such as Ashrae 52.2 (2012), Eurovent EN 779 (2012), ASTM F2100-11 and N95-98 for face masks. As is known in the industry, N stands for respirator filters that may be used when no oil is present in the contaminates and 95 identifies that filter has been tested and certified by the National Institute for Occupational Safety and Health (NIOSH) to have a filter efficiency level of 95% or greater against particulate aerosols. It is envisaged that the filtration efficiency of the filter media when tested against applicable N95-98 industry standards may be at least be N98 having a filtration rate of 98% to greater than 99%.

A nanofibre filter may be utilised in the composite filter media. The use of nanofibre filter technology may achieve higher efficiency for a particular filtration mechanism as stated above. The inventor has found that the use of nanofibre for most penetrating particle size (MPPS) particulate filtration and volatile organic compounds (VOCs) has the advantage of high efficiency with a low airflow resistance. Without being bound by theory, the high porosity with small pore sizes and large fibre surface area means the fine particles are trapped whilst still allowing air to pass. This has the effect of lower power requirements for the fan and extended filtration life.

It is envisaged that a functional nanofibre may be used that may include, but not be seen as limited to, antimicrobial, antibacterial and antiviral additives such as nano silver or manuka extract.

The composite filter media may utilise a gas phase adsorption filter or other type of gas phase filtration before removal of odour and/or noxious gases.

As known in the industry, gas phase adsorption is the process of using an adsorption media to adsorb gases and odours in an air stream. In one embodiment activated carbon or alumina or the like may be utilised for odour absorption and to remove or reduce the levels of gases and odours. As above, this may be used in conjunction with some other form of air filtration system or air filter (for example, nanofibre filter) to keep the carbon or other media from collecting particulates.

Gas phase adsorption may be utilised where a specific type of gas needs to be removed or reduced. It has been found that the thicker the filter, the longer the adsorptive media may be in contact with the gas.

Carbon and other adsorptive media may have a limited life and it has been found that they may only adsorb 33% to 50% of their weight before they lose their optimum efficiency and are replaced.

In a second aspect there is provided a respirator comprising:
 a face mask configured to cover the face of a user; and
 at least one air filter attached to the face mask and configured to filter unpurified air to provide breathable air;
 wherein
 the respirator also comprises a powered impeller unit mounted on the face mask and configured to compress and distribute the breathable air inside the face mask in an arc substantially parallel to the internal surface of the face mask; and
 the face mask forms a gap between an edge of the face mask and the user's face and configured to allow a positive flow of the breathable air together with exhaled air to exit the face mask and exclude ingress of external unpurified air.

The face mask may not form a seal around the face of the user. It may be attached to a user's eyewear and may not contact the face of the user. In this way, the face mask may not cause skin irritation and hence is more comfortable to a user to wear, the face mask may not need to be monitored to ensure a positive seal to keep out pollutants, and the user may not have to forcefully inhale or exhale against the pressure drop associated with a sealed system. Also, the above attachment points may not require contact to hair or top of the head, for increased comfort.

The face mask may be a half face mask configured to substantially cover the mouth and nose of the user. In other embodiments the face mask may be integrated into a full face mask with integral eye protection for the user.

The face mask may be manufactured out of a non porous material such as plastic, metal or carbon fibre. In this way, the face mask can be easily cleaned and may not absorb gases or other types of pollutants. Also, the material of the face mask may be dynamically flexible or rigidly solid as required. This allows the face mask to be easily interchanged and moulded to accommodate different sized faces and with the ability to aesthetically alter the look of the shield. For example, a face mask manufactured out of transparent material may improve visibility of facial expressions when users are communicating.

The face mask may include a moulded interior surface that allows a flow of air directed within the cavity of the face mask to radiate out to the peripheral edges of the face mask, thereby preventing a lateral mixing of external unpurified air into the interior of the face mask from the gap between the edge of the face mask and the user's face. In this way, a pocket of purified air is provided in front of the mouth and nose whilst also allowing for exhaled air to escape.

The face mask also comprises at least one adjustable gate configured to provide a controlled bleed of air from the internal cavity of the face mask to the eye region of the user. The interior mould surface of the face mask may control the direction of the bleed of air such that there is no high speed air blowing directly into eyes of the user. The bleed of purified air keeps the internal surface of the eyewear lenses from fogging, prevents contaminants contacting the eyes of the user and cools the eyes.

The eyewear may provide a conduit for electrical wiring from a power source, either by having wires embedded in the eyewear frame or by supporting the wires with a mechanical attachment to the eyewear frame.

An impeller unit may be positioned substantially centrally on the face mask in relation to the mouth of the user. An impeller unit may comprise an electric motor and an impeller rotor to form an air pump to create a positive pressure flow of air into the internal cavity of the face mask and exiting through the gap between the face mask and the user's face. In this way, the air pressure inside the cavity of the face mask is higher than the external air pressure and enables a continual flow of purified air without stopping or reversing back into the internal cavity of the face mask from the external atmosphere via the gap. The impeller unit may be unshrouded (not enclosed in a case) on an external side of the face mask, in order not to impede the drawing of external air. The drawn flow of air is purified by an associated purifying air filter. An impeller rotor compresses and distributes the flow of purified air emanating from the purifying air filter in a substantially 360° plane or arc substantially parallel to the internal surface of the face mask to curve the air around the user's mouth and nose to create a volume of filtered air in front of the user's mouth and nose which the user can safely breathe.

The fan supply unit may be powered by a battery. The battery may be rechargeable or replaceable and be of sufficient capacity to allow the respirator to operate for a desired period of time. In one embodiment the battery may be a lightweight lithium ion battery. Optionally a low battery indicator such as at least one LED bulb may indicate when the battery is low on power. The battery may be attached to the user via a battery attachment means such as a belt clip or neck dongle. The battery may be electrically attached to the eyewear via a power cord.

In alternative embodiments, the impeller unit may be powered from an external power source such as a vehicle battery or mains socket (12 volt DC, 240 volt AC power source) via an adapter.

The respirator may also comprise at least one air pressure sensor attached to the face mask and configured to monitor air pressure inside and outside the face mask to send an electrical signal to the impeller unit motor to vary the amount of power to the impeller rotor thereby controlling the speed of the impeller rotor to maintain positive air pressure within the interior cavity of the face mask.

It is envisaged that the dynamic pressure or positive pressure within the engineered gap of the face mask may range from 1-20 Pa. The inventor has found that an optimum pressure may be 5 Pa as the respirator allows for a continuous supply of purified air in the gap space and there is no requirement of a high positive pressure. However, this should not be seen as a limitation on the embodiments envisaged for this invention. If the external air becomes more hazardous to the user and/or this external air becomes more turbulent or "windy", then the positive pressure of the filtered air within the gap space of the face mask may be increased in order to prevent possible infiltration of the external air. Conversely, the pressure may be decreased depending on ambient conditions.

The gap may range from 15-100 cm$^2$, wherein the gap may be calculated from a supply air flow and bleed velocity respectively.

The supply air flow from a pump may range from 1-20 L/s or 0.001-0.20 m$^3$/s. The inventor has found that an optimum air flow may be 2-3 or up to 7 L/s or 0.002-0.003 up to 0.007 m$^3$/s. By way of example, an over-supply of air given heavy breathing may be considered to be approximately 0.5 L/s.

As above, the bleed velocity may be dependent on the area of the gap space. For example, the bleed velocity correlating to a particular gap space may be 0.5 m/s:100 cm$^2$, 1 m/s:50 cm$^2$, or 2 m/s:25 cm$^2$ respectively.

In one embodiment, the respirator may comprise an external moisture barrier filter for protection against the elements such as rain, and internal purifying air filter to filter impurities from the compressed air distributed by the impeller unit. Different types of filters that may work by various filtration mechanisms may include, but not be limited to, adsorption, absorption, size exclusion, interception, inertial impact, electrostatic attraction and diffusion (Van der Waals forces).

The discharged air from the fan supply unit may pass through the filter media and in doing so, any particulate matter, i.e. dust, pollen, etc. in the air may be retained on or in the filter media, at least down to the particle size limitation of the filter media used. The filter media used generally may be that with maximum porosity and yet may retain a sufficient percentage of the minimum size of the offending particles the user may want to avoid. In this way, the filter has the least resistance to air flow and therefore may require the least fan and power requirements and thereby the least size and weight overall, hence the filter media may be interchangeable and/or removable.

The filtration efficiency of the purifying air filter may at least meet applicable industry standards by those skilled in the art such as Ashrae 52.2 (2012), Eurovent EN 779 (2012), ASTM F2100-11 and N95-98 for face masks. As is known in the industry, N stands for respirator filters that may be used when no oil is present in the contaminates and 95 identifies that filter has been tested and certified by the National Institute for Occupational Safety and Health (NIOSH) to have a filter efficiency level of 95% or greater against particulate aerosols. It is envisaged that the filtration efficiency of the filter media when tested against applicable N95-98 industry standards may be at least be N98 having a filtration rate of 98% to greater than 99%.

A nano-fibre filter may be utilised in the composite filter media. The use of nano-fibre filter technology may achieve higher efficiency for a particular filtration mechanism as stated above.

The inventor has found that the use of nano-fibre for most penetrating particle size (MPPS) particulate filtration and volatile organic compounds (VOCs) has the advantage of high efficiency with a low airflow resistance. Without being bound by theory, the high porosity with small pore sizes and large fibre surface area means the fine particles are trapped whilst still allowing air to pass. This has the effect of lower power requirements for the fan and extended filtration life.

It is envisaged that a functional nano-fibre may be used that may include, but not be seen as limited to, antimicrobial, antibacterial and antiviral additives such as nano silver or manuka extract.

The composite filter media may utilise a gas phase adsorption filter or other type of gas phase filtration before removal of odour and/or noxious gases.

As known in the industry, gas phase adsorption is the process of using an adsorption media to adsorb gases and odours in an air stream. In one embodiment activated carbon or alumina or the like may be utilised for odour absorption and to remove or reduce the levels of gases and odours. As above, this may be used in conjunction with some other form of air filtration system or air filter (for example, nano-fibre filter) to keep the carbon or other media from collecting particulates.

Gas phase adsorption may be utilised where a specific type of gas needs to be removed or reduced. It has been found that the thicker the filter the longer the adsorptive media may be in contact with the gas.

Carbon and other adsorptive media may have a limited life and it has been found that they may only adsorb 33% to 50% of their weight before they lose their optimum efficiency and are replaced.

The face mask also may comprise at least one releasable attachment means for a user's eyewear. In one embodiment the releasable attachment means may be at least one magnet positioned on the face mask and if required a corresponding magnetic strip on the eyewear, a helmet or the like configured to provide a snap fit of the user's eyewear or helmet to the face mask. The magnet also may provide the functionality of an electrical connection between a battery and the powered impeller unit.

The magnets may be embedded during manufacture of the face mask or be modified after production to have magnets mechanically affixed.

In one embodiment, the at least one releasable attachment may be two releasable attachments positioned on a top edge of the face mask proximal the user's eyes and configured to attach to a lower edge of each lens of the eyewear. In this way, the eyewear is stabilised on the face mask. The eyewear can be detached and reattached to the respirator quickly in seconds if required without reattaching the respirator or adjusting its fit once head mounted.

A further releasable attachment means may include a nose piece that helps keep the face mask centred in the required position on the user's face region.

The eyewear may either be safety glasses, corrective lens glasses or half lens frames.

The respirator may also be upgraded with other wearable technologies such as air contaminant sensors, wireless audio headphones, microphones and/or an optical head up display or the like.

In a third aspect there is provided a respirator comprising:
an air delivery system for generation of a positive flow of air;
a face mask configured to cover the face of a user; and
the face mask forms a gap between an edge of the face mask and the user's face and configured to allow the positive flow of breathable air together with exhaled air to exit the face mask and exclude ingress of external unpurified air;
wherein
the gap between the edge of the face mask and the user's face closes to form a seal when air pressure inside the mask drops to a predetermined level.

The above describes a floating seal configuration which may be useful in a noxious gas or other such deadly environments.

The gap between the edge of the face mask and the user's face may close and form a seal when activated by a mechanical and/or electrical malfunction or the like. For example, such as a battery fault, or fan failure.

The seal may comprise a strip of flexible material on at least one edge of the mask or shield that may be held away from the face by positive air pressure or mechanical means. The elasticity of the material or mechanical means may pull the mask towards the face to form the seal when air pressure inside the mask drops below a predetermined level.

Advantages of the above include:
A compact, self-contained and portable respirator with portable air delivery system having a battery power source which provides breathable purified air to the user;
An easily detachable or removable face mask or shield manufactured out of a non porous material so that the face shield is easily cleaned and does not absorb gases or other types of pollutants;
A face shield manufactured out of dynamically flexible or rigidly solid material that is interchangeable and moulded to accommodate different sized faces or to aesthetically alter the look of the shield;
A moulded interior surface of the face shield allows a flow of air directed within the cavity of the face shield to radiate out thereby preventing a venturi effect entraining outside air and provides a control of bleed air to the exterior or design spaces. In this way, a pocket of purified air is created in front of the mouth and nose whilst also allowing for exhaled air to escape. An advantage of the interior mould surface is that it controls the direction of the bleed air such that there is no high speed air blowing into the eyes of the wearer;
An integrated powered impeller unit which is mounted on the face mask and configured to compress and distribute filtered breathable air inside the face mask at a higher pressure than the external air and in a substantially 360° plane or arc substantially parallel to the internal surface of the face mask to create a pocket of purified air is created in front of the mouth and nose;

A gap between the edge of the face mask and the users face allows exhaled air to escape and together with the powered impeller unit provides a positive flow of air through the face mask which prevents lateral ingress of unpurified external air from entering the gap;

A moulded interior surface of the face mask which together with the impeller unit allows a flow of air directed within the cavity of the face mask to radiate out thereby preventing a lateral inflow of unpurified air into the interior of the face mask and providing a control of bleed air to the exterior eye region. An advantage of the interior mould surface is that it controls the direction of the bleed air such that there is no high speed air blowing into the eyes of the user;

An arm or side member with a hollow section provides an attachment point for the integral air supply line to the face shield thereby minimising components of the respirator and hence reduced manufacturing costs and a more streamlined aesthetic appearance;

A foldable arm to allow for ease of storage when the respirator is not in use;

A mechanism for adjustment for both width and length of the arms that rest on top of the ear. In this way, the fitment of the face shield is easily accommodated to suit the size and shape of a wearer's face;

A face mask does not contact the face region nor form a seal around the face region of the user which provides the advantage of improved user comfort (no skin irritation and hence more comfortable to wear), the face mask does not need to be monitored to ensure a positive seal to keep out pollutants (hence also effective for users with facial hair), and the user does not have to forcefully inhale or exhale against the pressure drop associated with a sealed system;

Releasable attachment points on a user's eyewear that support and retain the face mask on a face region of a user which provides the advantage of improved ease of use in removing the face mask if needed and repositioning on a user's face without the need to adjust head straps;

An engineered cavity within the mask and gap area is advantageously dimensioned to optimise supply air flow, bleed velocity such that a pocket of purified air in front of the mouth and nose is created whilst also allowing for exhaled air to escape;

A minimal design which reduces manufacturing costs and provides a more streamlined aesthetic appearance;

A motor and pressure sensor that are very close to the mouth and nose. An advantage of this is that when the user takes a sharp inhalation of breath, the close proximity of the motor and the very small air column enable the system to respond very quickly to maintain positive pressure, and ensure that the direction of the air flow is not reversed by breathing in; and A safety feature that includes a floating seal for use in deadly environments or mechanical/electrical malfunction.

The embodiments described above may also be said broadly to consist in the parts, elements and features referred to or indicated in the specification of the application, individually or collectively, and any or all combinations of any two or more said parts, elements or features.

Further, where specific integers are mentioned herein which have known equivalents in the art to which the embodiments relates, such known equivalents are deemed to be incorporated herein as if individually set forth.

WORKING EXAMPLES

The above described respirator apparatus, operation and uses thereof are now described by reference to specific examples.

Example 1

Respirator with Rear Integrated Air Delivery System

Figure 1:
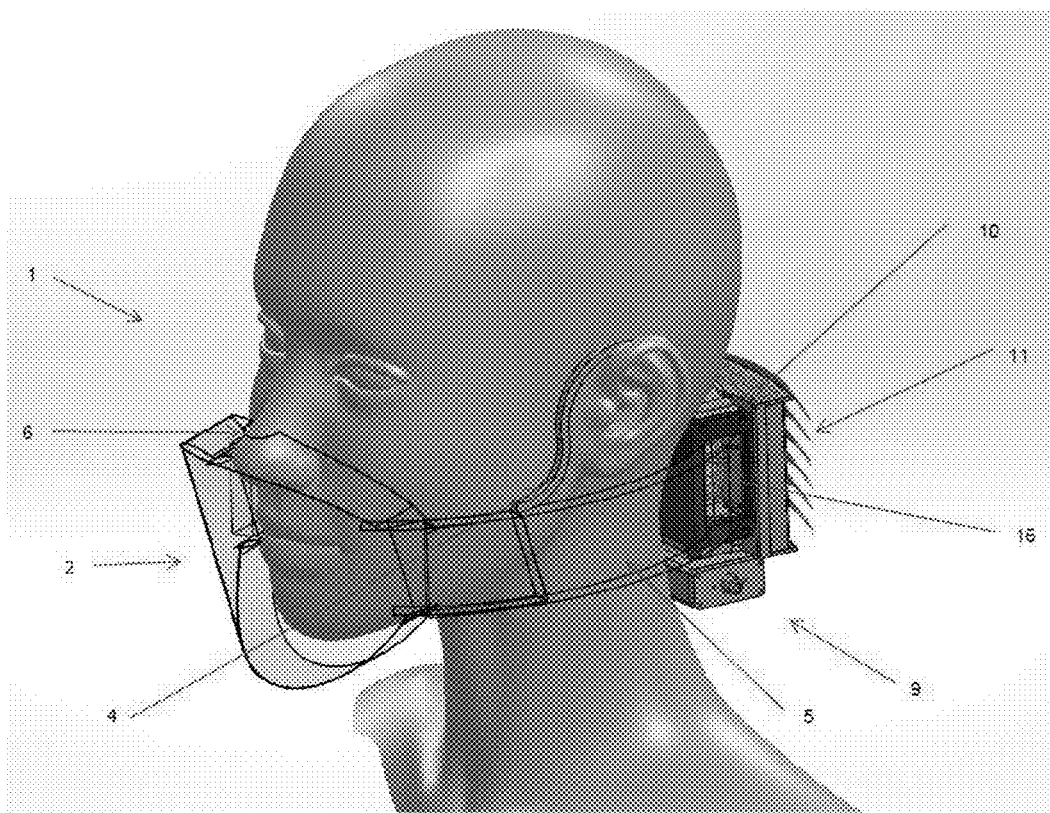
FIG. 1 illustrates a front perspective view of one embodiment of a respirator with rear integrated air delivery system being worn by a user.

With reference to FIGS. 1, 2 and 3, a perspective, front and side view of a respirator apparatus 1 respectively is shown that includes a detachable face shield 2 manufactured out of a moulded non porous material. The face shield 2 includes a moulded interior surface that allows a flow of air directed within a cavity 3 (best seen in FIG. 5) of the face shield 2 to radiate out thereby preventing a venturi effect entraining outside air and provides a controlled bleed of the air to the exterior. An arm member or ear hook 4 extends over the ear to help hold the face shield 2 in place and is foldable to allow for ease of storage when the respirator 1 is not in use. Also, the arm member 4 is attached to an integrated air supply line 5 to the face shield 2. A nose piece 6 keeps the face shield 2 in a required position on the wearer's face region. In particular, the two arm members 4 and nose piece 6 ensure that the face shield 2 does not contact the face region nor form a seal around the face region of the wearer.

As shown, the face shield 2 includes an eye air deflector 7 for deflecting air away from a wearer's eyes.

The air supply line 5 that is in fluid communication with the face shield 2 is a clear hollow plastic material and configured to allow for an integrated dual air line 5 configuration on either side of the wearer's head such that a positive stream of laminar flow of air is provided on each side of the face shield 2. In one embodiment, a jet nozzle (not shown) is attached to a distal end of the air supply line 5 such that the positive stream of laminar flow is directed to the intersection region 8 (best seen in FIG. 5) within the cavity 3 of the face shield 2. The gap area (not shown) ranges from 10-100 cm$^2$, and is calculated from the supply air flow and bleed velocity respectively (see calculations further below).

The respirator 1 includes an air delivery system or fan supply unit comprising an electric motor and an impellor or fan 16 to create an air pump, all housed within a pump housing. The air delivery system is integrally attached to the air supply line 5 which is located about the rear neck region of a wearer. The air delivery system is powered by a rechargeable battery 9 housed within or located about the air delivery system and is of sufficient capacity to allow the respirator 1 to operate for a continuous period of six hours or more.

The air delivery system or fan supply unit includes a filter media or a filtration system comprising a filter housing 10, rain deflector 11, nanofilter 12 and an activated carbon gas phase adsorption filter (not shown) for removal of particulates, odour and/or noxious gases respectively, again all contained within the air delivery system.

The respirator 1 is configured to operate as follows:

A positive pressure flow of air is generated by the air delivery system to the respirator 1 and the air flow and positive pressure is regulated, in part, by adjusting the fan 16 speed. The discharged air from the air delivery system passes through the composite filter media and in doing so, any particulate matter, i.e. dust, pollen, etc. in the air is retained on or in the filter media, at least down to the particle size limitation of the filter media used.

The fan 16 is regulated so that the discharged air from the filter media flows through the air supply line 5 at 5 L/s or 0.005 m$^3$/s. The discharged purified air travels through the dual air feed supply line 5 on either side of the wearer's head such that a positive stream of laminar flow of air is provided on each side of the face shield 2.

With reference to FIG. 5, the two streams of laminar flow of filtered air 13 collide at an intersection region 8 within a cavity 3 of the face shield 2 to create a turbulent flow of air 14 or diffuse pocket of air that radiates away from the intersection region 8 therein. This creates an over-pressure of clean filtered air around the mouth and nose. The over-pressure air then flows towards and out of the gap area (bleed air) along with exhaled air between the shield and face. The combination of bleed air and exhaled air both prevent ingress of polluted air. The interior mould surface of the face shield 2 controls the direction of the bleed of air such that there is no high speed air blowing into eyes of the wearer. It is envisaged that the dynamic pressure or positive pressure within the engineered gap area of the face shield is 5 Pa as the respirator 1 allows for a continuous supply of purified air in the cavity and gap area and there is no requirement of a high positive pressure. However, if the outside air becomes more hazardous to the wearer and/or this outside air becomes more turbulent or "windy", then the positive pressure of the filtered air within the cavity and gap area of the face shield is increased in order to prevent possible infiltration of the outside air. Conversely, the pressure is decreased depending on ambient conditions. The above change in pressure is regulated by a pressure sensor 15 mounted within the face shield 2.

As above, the bleed air velocity is dependent on the gap area. For example, the bleed velocity is 0.5 m/s, 1 m/s, or 2 m/s for a given gap space of 100 cm$^2$, 50 cm$^2$, or 25 cm$^2$ respectively (see calculations below).

Example 2

Respirator with Dual Integrated Air Delivery System

With reference to FIGS. 7, 8 to 10, a rendered side, front, side and rear view of a respirator apparatus 1 respectively is shown that includes a detachable face shield 2 manufactured out of a moulded non porous material. The face shield 2 includes a moulded interior surface that allows a flow of air directed within a cavity 3 (best seen in FIG. 5) of the face shield 2 to radiate out thereby preventing a venturi effect entraining outside air and provides a controlled bleed of the air to the exterior. An arm member or ear hook 4 extends over the ear to help hold the face shield 2 in place and is foldable via a hinge 17 to allow for ease of storage when the respirator 1 is not in use (bet seen in FIGS. 11 and 12). Also, the arm member 4 is attached to an integrated air supply line 5 to the face shield 2. A nose piece (not shown) keeps the face shield 2 in a required position on the wearer's face region. In particular, the two arm members 4 and nose piece ensure that the face shield 2 does not contact the face region nor form a seal around the face region of the wearer.

As shown, the face shield 2 includes an eye air deflector 7 for deflecting air away from a wearer's eyes.

The air supply line 5 that is in fluid communication with the face shield 2 is a clear hollow plastic material and configured to allow for an integrated dual air line configuration on either side of the wearer's head such that a positive stream of laminar flow of air 13 is provided on each side of the face shield 2. In one embodiment, a jet nozzle (not shown) is attached to a distal end of the air supply line 5 such that the positive stream of laminar flow 13 is directed to the intersection region 8 (best seen in FIG. 5) within the cavity 3 of the face shield 2. The gap area (not shown) ranges from 10-100 cm$^2$, and is calculated from the supply air flow and bleed velocity respectively (see calculations further below).

The respirator 1 includes dual air delivery systems or fan supply units each comprising an electric motor and an impellor or fan 16 to create an air pump, all housed within a pump housing. The dual air delivery systems are integrally attached to the air supply line 5 which are located about each side below the ears of a wear's head. Each air delivery system is powered by a rechargeable battery 9 located about the air delivery system and is of sufficient capacity to allow the respirator 1 to operate for a continuous period of six hours or more.

Each air delivery system or fan supply unit includes a filter media or a filtration system comprising a filter housing 10, rain deflector 11, nanofilter 12 and an activated carbon gas phase adsorption filter (not shown) for removal of particulates, odour and/or noxious gases respectively, again all contained within the air delivery system.

The respirator 1 is configured to operate as previously described above for Example 1 and need not be described again.

Example 3

Respirator with Separate Air Delivery System

With reference to FIGS. 13, 14 to 16, a perspective, front and side and rear view of a respirator apparatus 1 respectively is shown that includes a detachable face shield 2 manufactured out of a moulded non porous material. The face shield 2 includes a moulded interior surface that allows a flow of air directed within a cavity 3 (best seen in FIG. 5) of the face shield 2 to radiate out thereby preventing a venturi effect entraining outside air and provides a controlled bleed of the air to the exterior. An arm member or ear hook 4 extends over the ear to help hold the face shield 2 in place and is foldable to allow for ease of storage when the respirator 1 is not in use. Also, the arm member 4 is attached to a hollow plastic side member 19 that provides an integrated air supply line 5 to the face shield 2. A nose piece (not shown) keeps the face shield 2 in a required position on the wearer's face region. In particular, the two arm members 4 and nose piece ensure that the face shield 2 does not contact the face region nor form a seal around the face region of the wearer.

As shown, the face shield 2 includes an eye air deflector 7 for deflecting air away from a wear's eyes.

The air supply line 5 that is in fluid communication with the hollow side members 19 is a clear flexible silicon hose attached to an air delivery system or fan supply unit configured to extend up to a manifold 18. The manifold 18 allows a dual air line configuration for integration into each side member 19 on either side of the wearer's head such that a positive stream of laminar flow of air 13 is provided on each side of the face shield 2. In one embodiment, a jet nozzle (not shown) is attached to a distal end of each side member 19 such that the positive stream of laminar flow 13 is directed to the intersection region 8 (best seen in FIG. 5) within the cavity 3 of the face shield 2. The gap area (not shown) ranges from 10-100 cm², and is calculated from the supply air flow and bleed velocity respectively (see calculations further below).

The respirator 1 includes an air delivery system or fan supply unit comprising an electric motor and a fan 16 to create an air pump, all housed within the pump housing. The fan supply unit or air delivery system is attached to a wearer's pocket or fastened to a belt or some other convenient place by fastener such as a clip (not shown). The air delivery system is powered by a rechargeable battery 9 housed within the air delivery system and is of sufficient capacity to allow the respirator 1 to operate for a continuous period of six hours or more.

The air delivery system or fan supply unit includes a filter media or a filtration system comprising a filter housing 10, nanofilter 12 and an activated carbon gas phase adsorption filter (not shown) for removal of particulates, odour and/or noxious gases respectively, again all contained within the air delivery system.

The respirator 1 is configured to operate as previously described for Examples 2 and 3 above, and need not be described again.

Example 4

Respirator with Front Integrated Air Delivery System

With reference to FIGS. 17 and 18, a respirator 1 for a user is shown that includes a detachable protective eyewear 20 and a face mask 2 manufactured out of a moulded non porous material. The face mask 2 includes a moulded interior surface that allows a flow of air directed within a cavity 3 (best seen in FIG. 24) of the face mask 2 to radiate out to the outer edges of the face mask 2 thereby preventing an in-flow of external air into the interior of the face mask 2 and providing a controlled bleed of the air to the exterior. The face mask also includes at least one adjustable gate 21 configured to allow the user to control the bleed of air from the internal cavity 3 of the face mask to the eyewear 20.

Attachment points 22 enable a magnetic snap fit to the eyewear 20 in the form of full face glasses (such as safety and/or prescription glasses) 20 to ensure that the face mask 2 is positioned over a user's mouth and nose but does not contact the face region nor form a seal around the face region of the user.

The air supply to the respirator 1 is filtered by means of an external moisture filter 23 to prevent ingress of water from rain or the like into the cavity 3 of the face mask 2. An internal nanofilter 12 in the form of a N98 filter, filters the dry air from the moisture filter 23 to provide purified breathable air by removal of odour and/or noxious gas particles.

The respirator 1 includes a powered impeller unit 16 mounted on the face mask 2 and comprising an impeller motor and rotor (not shown) to compress the in-flowing air and distribute it in a 360° plane or arc parallel to the internal surface of the face mask 2.

A gap 24 allows positive flow of purified air and of exhaled air but prevents lateral mixing of external unpurified air by ingress through the gap 24 into the cavity 3. The gap 24 area ranges from 15-100 cm², and is calculated from the supply air flow and bleed velocity respectively (see calculations further below).

The impeller unit 16 is powered by a power supply in the form of a lightweight lithium ion battery 9 on board. The battery 9 may be various sizes and capacities depending on the needs of the user. For example, the battery 9 may have sufficient capacity to allow the respirator 1 to operate for up to two hours which may be useful in a situation where the respirator 1 is being used for short periods of time and a more compact battery 9 is preferred. Alternatively a larger battery 25 or external power source 28 may be utilised to enable continuous operation for a period of six hours or more.

The battery 25 is electrically connected to the impeller unit 16 via a power cord 26. The rotor of the impeller unit 16 is adjustable by a control indicated in the region on the face mask by label 27.

An external and internal air pressure sensor 15 is configured to monitor the air pressure outside and inside the face mask 2 and sends an electrical signal to the impeller unit 16 thereby controlling the speed of the impeller rotor (not shown).

In use and with reference to FIGS. 19 and 20, the respirator 1 is configured to operate as follows:

A positive pressure flow of air is generated by the impeller unit 16 of the respirator 1 compressing and distributing filtered air from the nanofilter 12. The air flow and positive pressure is regulated, in part, by adjusting the impeller 16 rotor speed. By passing the discharged air from the impeller unit 16 through the nanofilter 12, any particulate matter, i.e. dust, pollen, etc. in the air is retained on or in the filter media, at least down to the particle size limitation of the filter media used.

The impeller unit 16 is regulated so that the discharged air flows at 5 L/s or 0.005 m³/s.

This creates an overpressure of clean filtered air around the mouth and nose. The overpressure air, or bleed air, then flows towards and out of the gap 24 along with exhaled air between the shield and face. The combination of bleed air and exhaled air both prevent ingress of polluted air. The interior surface of the face mask 2 controls the direction of the bleed of air such that there is no high speed air blowing into eyes of the user. It is envisaged that the dynamic pressure or positive pressure within the engineered gap of the face mask is 5 Pa as the respirator 1 allows for a continuous supply of purified air in the cavity 3 and gap 24. However, if the external air becomes more hazardous to the user and/or this external air becomes more turbulent or "windy", then the positive pressure of the filtered air within the cavity and gap of the face mask is increased in order to prevent possible infiltration of the external air. Conversely, the pressure is decreased depending on ambient conditions.

As above, the bleed air velocity is dependent on the gap 24. For example, for an airflow of 5 L/s the bleed velocity is 0.5 m/s, 1 m/s, or 2 m/s for a given gap space of 100 cm², 50 cm², or 25 cm² respectively (see calculations below).

With reference to FIGS. 21 and 22, the user's eyewear 20 in an alternative embodiment may be half frame glasses 20.

With reference to FIG. 23, the magnetic attachment points 22 aid in stabilising and positioning the face mask 2 in relation to the eyewear 20.

With reference to FIG. 24, the impeller unit 16 is shrouded on the internal cavity side of the face mask 2 by the nano-fibre filter 12. A mouth guard 29 prevents contact of the filter 12 and impeller unit 16 with the user's mouth.

Example 5

Respirator with a Floating Seal

With reference to FIG. 25, a respirator 1 is shown where the face mask comprising flexible 30 and rigid 31 material portions forms a gap between an edge of the face mask 2 and the user's face under positive air pressure. This configuration is referred to as a floating seal that comprises a strip of flexible material 30 on at least one edge of the mask or shield 2.

As noted above, the floating seal is held away from the face by positive air pressure. The elasticity of the material 30 pulls the mask towards the face to form the seal i.e. the gap closes when the air pressure inside the mask drops below a predetermined level as shown in FIG. 26.

A floating seal configuration is used for the above described respirators 1 in a noxious gas or other such deadly environments. Also, the gap is closed or triggered when activated by a mechanical and/or electrical malfunction or the like.

Exemplary Calculation

The following calculations may be used to determine the relationship between bleed velocity, pressure and through area (gap space).

ƥ =Density air 1.2 kg/m
P (Dynamic pressure)= ƥ ×V² (velocity) m/s
Q (airflow)=V×A where Q is in m³/s, V is m/s and A is m²

Air is continually being refreshed in the cavity or pocket, hence there is no requirement for a high positive pressure. Optimally, there is 5 Pa pressure (P) in the cavity or pocket.

The gap space (through area A) is calculated using a bleed velocity (V) of 0.5 m/s and a supply airflow (Q) of 5 L/s or 0.005 m³/s Therefore, the through area is calculated as follows:

$$0.005/0.5 = 0.01 \text{ m}^2 \text{ or } 100 \text{ cm}^2$$

Therefore, it correlates that if the bleed velocity is doubled, then the through area is halved i.e. for 1 m/s bleed velocity, through area (gap)=50 cm².

The bleed velocity required to achieve a given pressure in the cavity or pocket is calculated as follows: V²=P/ƥ. For the optimal pressure of 5 Pa, V²=5/1.2 so V=2 m/s.

Therefore, it correlates that if the bleed velocity is halved, then the pressure decreases by a factor of 4 i.e. for 1 m/s bleed velocity, pressure=1.2 Pa.

- Bleed velocity of 0.5 m/s for gap of 100 cm² (P=0.3 Pa)—maximum gap space for effective operation;
- Bleed velocity of 1 m/s for gap of 50 cm² (P=1.2 Pa); and
- Bleed velocity of 2 m/s for gap of 25 cm² (P=4.8 Pa)—optimal conditions.

Aspects of the present have been described by way of example only and it should be appreciated that modifications and additions may be made thereto without departing from the scope of the invention as claimed herein.

What is claimed is:

1. A respirator comprising:
a face shield shaped and adapted for attaching to a face region of a wearer, the face shield comprising a curved interior surface;
at least two substantially opposing air supply lines in fluid communication with the face shield, wherein the curved interior surface of the face shield defines a curved path between the at least two opposing air supply lines for positive streams of laminar flow of air; and
an air filter for filtration of the laminar flow of air,
wherein the at least two opposing air supply lines are spaced apart and directed to allow the streams of the laminar flow of filtered air to collide at an intersection region within a cavity of the face shield creating a turbulent flow of air that radiates away from the intersection region therein for supplying filtered breathing air to a wearer's face region and exclusion of outside unpurified air, wherein the face shield does not form a seal around the face region of the wearer, wherein the face shield is shaped to avoid covering an eye region of the wearer when attached to the face region, and wherein the face shield interior surface is molded to allow the turbulent flow of air within the cavity of the face shield to radiate out thereby preventing a venturi effect entraining outside air and providing a control of bleed air to the exterior.

2. The respirator as claimed in claim 1, wherein the face shield is removable and manufactured out of a non porous material.

3. The respirator as claimed in claim 1, further comprising an arm or side member that is hollow to provide an integrated air supply line to the face shield.

4. The respirator as claimed in claim 1, wherein the face shield provides an attachment point to support and retain the face shield on a face region of a wearer, wherein the face shield does not contact the face region nor form a seal around the face region of the wearer.

5. The respirator as claimed in claim 1, wherein a first jet nozzle is spaced at an engineered distance apart from a corresponding second jet nozzle attached to distal ends of air lines such that the positive streams of laminar flow of air are directed to the intersection region within the cavity of the face shield.

6. The respirator as claimed in claim 1, wherein a dynamic pressure or positive pressure within an engineered gap area of the face shield ranges from 1-20 Pa.

7. The respirator as claimed in claim 6, wherein the engineered gap area ranges from 10-100 cm², and wherein the engineered gap area is calculated from a supply air flow and bleed velocity respectively.

8. The respirator as claimed in claim 7, wherein the supply air flow from a pump ranges from 1-9 L/s.

9. The respirator as claimed in claim 1, wherein the respirator comprises at least one air pressure sensor to maintain positive air pressure within the cavity of the face shield.

10. The respirator as claimed in claim 1, wherein the respirator includes at least one air delivery system.

11. A respirator comprising:
a face mask configured to cover the face of a user and avoid covering an eye region of the face, the face mask comprising a curved interior surface; wherein the face mask is configured to form an engineered gap between an edge of the face mask and the face of the user when the face mask is worn;
at least one air filter attached to the face mask and configured to filter unpurified air to provide breathable air;
wherein the respirator further comprises a powered impeller unit mounted on the face mask, the impeller unit being oriented to emit the breathable air inside the face mask in a substantially 360 degree plane;
wherein the face mask includes a moulded interior surface that allows a flow of air directed within an internal cavity of the face mask to radiate out in an arc substantially parallel to the curved interior surface of the face mask to peripheral edges of the face mask thereby preventing a lateral mixing of external unpurified air into the interior of the face mask from the engineered gap between the edge of the face mask and the face of the user; and wherein the engineered gap is configured to allow a positive flow of the breathable air together with exhaled air to exit the face mask and exclude ingress of external unpurified air.

12. The respirator as claimed in claim 11, wherein the face mask comprises at least one adjustable gate configured to provide a controlled bleed of air from the internal cavity of the face mask to the eye region of the user.

13. The respirator as claimed in claim 11, wherein the impeller unit is positioned substantially centrally on the face mask to create a positive pressure flow of air into the internal cavity of the face mask and exiting through the engineered gap between the face mask and the face of the user.

14. The respirator as claimed in claim 11, wherein the respirator comprises at least one air pressure sensor attached to the face mask and configured to monitor air pressure inside and outside the face mask.

15. The respirator as claimed in claim 11, wherein a dynamic pressure or positive pressure within the engineered gap of the face mask ranges from 1-20 Pa.

16. The respirator as claimed in claim 11, wherein the engineered gap ranges from 15-100 cm$^2$, and wherein the engineered gap is calculated from a supply air flow and bleed velocity respectively.

17. The respirator as claimed in claim 11, wherein discharged air from the impeller unit passes through a filter media or a filtration system.

18. The respirator as claimed in claim 11,
wherein the engineered gap between the edge of the face mask and the face of the user closes to form a seal when air pressure inside the face mask drops to a predetermined level.

* * * * *